United States Patent [19]

Varma et al.

[11] Patent Number: 5,089,523
[45] Date of Patent: Feb. 18, 1992

[54] FLUORINATED DERIVATIVES OF MEVINIC ACIDS

[75] Inventors: Ravi K. Varma, Belle Mead; Sam T. Chao, East Windsor, both of N.J.

[73] Assignee: E. R. Squibb & Sons, Inc., Princeton, N.J.

[21] Appl. No.: 521,880

[22] Filed: May 11, 1990

[51] Int. Cl.$^5$ .................. A61K 31/365; C07D 309/30
[52] U.S. Cl. .................... 514/460; 514/510; 549/292; 560/119
[58] Field of Search ........... 549/292; 560/119; 514/460, 510

[56] References Cited

U.S. PATENT DOCUMENTS

| | | | |
|---|---|---|---|
| 4,346,227 | 8/1982 | Terahara et al. | 560/119 |
| 4,410,629 | 10/1983 | Terahara et al. | 435/146 |
| 4,444,784 | 4/1984 | Hoffman et al. | 424/279 |
| 4,448,979 | 5/1984 | Terahara et al. | 549/292 |
| 4,450,171 | 5/1984 | Hoffman et al. | 424/279 |
| 4,499,289 | 2/1985 | Baran et al. | 549/292 |
| 4,719,229 | 1/1988 | Reamer et al. | 514/460 |

FOREIGN PATENT DOCUMENTS

| | | |
|---|---|---|
| 0065835 | 12/1982 | European Pat. Off. . |
| 0137444 | 4/1985 | European Pat. Off. . |
| 0251625 | 1/1988 | European Pat. Off. . |
| 0306210 | 3/1989 | Eoropean Pat. Off. . |
| 2075013A | 11/1981 | United Kingdom . |

OTHER PUBLICATIONS

F. M. Singer et al., Proc. Soc. Exper. Biol. Med., 102, 370-372, (1959).

Primary Examiner—Alan L. Rotman
Assistant Examiner—Ba K. Trinh
Attorney, Agent, or Firm—Timothy J. Gaul

[57] ABSTRACT

Compounds of the formula

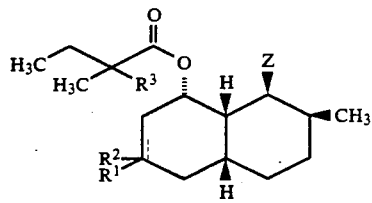

and pharmaceutically acceptable salts and tautomeric mixtures thereof possess activity as HMg–CoA reductase inhibitors, thus making them useful as antihypercholesterolemic agents. In the above formula, Z is

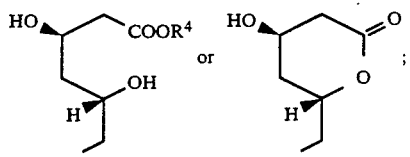

$R^1$ and $R^2$ are each independently fluoro or hydrogen, except that at least one of $R^1$ and $R^2$ is fluoro;
$R^3$ is hydrogen, alkyl, cycloalkyl, aryl or arylalkyl; and
$R^4$ is hydrogen, alkyl, ammonium, alkylammonium, or alkali metal.

10 Claims, No Drawings

FLUORINATED DERIVATIVES OF MEVINIC ACIDS

FIELD OF THE INVENTION

The present invention relates to fluorinated derivatives of mevinic acids that are HMG-CoA reductase inhibitors useful as antihypercholesterolemic agents.

BRIEF DESCRIPTION OF THE INVENTION

In accordance with the present invention, compounds of the formula

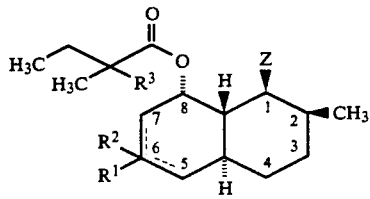

I and pharmaceutically acceptable salts and tautomeric mixtures thereof possess activity as HMG-CoA reductase inhibitors, thus making such compounds useful as antihypercholesterolemic agents. In formula I and throughout this specification, the above symbols are defined as follows:

Z is

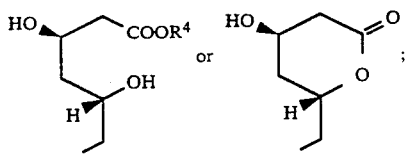

$R^1$ and $R^2$ are each independently fluoro or hydrogen, except that at least one of $R^1$ and $R^2$ is fluoro;

$R^3$, alkyl, cycloalkyl, aryl or arylalkyl; and $R^4$ is hydrogen, alkyl, ammonium, alkylammonium (such as triethylammonium), or alkali metal (such as Na, Li, or K).

A single or double bond may be present either between carbon 5 and carbon 6 or between carbon 6 and carbon 7, except that carbons 5 to 6 and 6 to cannot both be double-bonded.

DETAILED DESCRIPTION OF THE INVENTION

Listed below are definitions of various terms used to describe this invention. These definitions apply to the terms as they are used throughout this specification (unless otherwise limited in specific instances) either individually or as part of a larger group.

The term "alkyl" or "alk" includes both straight and branched chain radicals of up to carbons, preferably 1 to 8 carbons. Exemplary alkyl groups are methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl, the various branched chain isomers thereof, and the like. The term "alkyl" or "alk" also includes such groups having a halo-substituent, such as F, Br, Cl or I or $CF_3$, an alkoxy substituent, an aryl substituent, an alkyl-aryl substituent, a haloaryl substituent, a cycloalkyl substituent or an alkylcycloalkyl substituent.

The term "cycloalkyl" includes saturated cyclic hydrocarbon groups containing 3 to 12 carbons, preferably 3 to 8 carbons, which include cyclopropyl, cyclobutyl, cyclopentyl, cyclohexyl, cycloheptyl, cyclooctyl, cyclodecyl and cyclododecyl, wherein such groups may be substituted with 1 or 2 halogens, 1 or 2 lower alkyl groups and/or 1 or 2 lower alkoxy groups.

The term "aryl" or "Ar" as employed herein refers to monocyclic or bicyclic aromatic groups containing 6 or 10 carbons in the ring portion, such as phenyl or naphthyl, substituted phenyl or substituted naphthyl, wherein the substituent on either the phenyl or naphthyl may be 1 or 2 lower alkyl groups, 1 or 2 halogens (Cl, Br or F), and/or 1 or 2 lower alkoxy groups.

The term "halogen" or "halo" refers to fluorine, chlorine, bromine and iodine, as well as trifluoromethyl.

Preferred compounds of formula I are those wherein:
$R^3$ is hydrogen or alkyl (methyl most preferred);
Z is

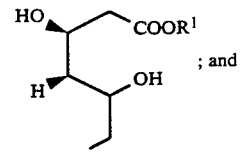

; and $R^4$ is hydro alkali metal (lithium most preferred).

The compounds of formula I will be formulated with a pharmaceutical vehicle or diluent. The pharmaceutical composition can be formulated in a classical manner with solid or liquid vehicles or diluents and pharmaceutical additives appropriate to the desired mode of administration. The compounds can be administered by an oral route (e.g., tablets, capsules, granules or powders) or a parenteral route (e.g., injectable preparations).

A typical capsule for oral administration contains active ingredients (25 mg), lactose (75 mg) and magnesium stearate (15 mg). The mixture is passed through a 60-mesh sieve and packed into a No. 1 gelatin capsule.

A typical injectable preparation is produced by aseptically placing 25 mg of a water-soluble salt of sterile active ingredient into a vial, aseptically freeze-drying and sealing. For use, the contents of the vial are mixed with 2 ml of physiological saline, to produce an injectable preparation.

The compounds of the invention are inhibitors of 3-hydroxy-3-methylglutaryl coenzyme A (HMG-CoA) reductase and inhibit cholesterol biosynthesis.

Such compounds are useful in treating atherosclerosis to inhibit progression of disease, in treating hyperlipidemia to inhibit development of atherosclerosis, and in treating nephrotic hyperlipidemia. In addition, the compounds of the invention increase plasma high density lipoprotein cholesterol levels. As HMG-CoA reductase inhibitors, the compounds of the invention may also be useful in inhibiting formation of gallstones and in treating tumors.

The compounds of the present invention may also be employed in combination with antihyperlipoproteinemic agents, such as probucol, and/or with one or more serum cholesterol lowering agents such as Lopid ® (gemfibrozil), bile acid sequestrants such as cholestyramine, colestipol, DEAE-Sephadex ® as well as clofibrate, nicotinic acid and its derivatives, neomycin, p-aminosalicylic acid, lovastatin, pravastatin, visinolin (velostatin, symvastatin or sinvinolin) and the like, and/or one or more squalene synthetase inhibitors.

The above compounds to be employed in combination with the HMG-CoA reductase inhibitor of the invention will be used in amounts as indicated in the Physicians' Desk Reference (PDR).

The dose to be administered depends on the unitary dose, the symptoms, and the age and the body weight of the patient. A dose for adults is preferably between 20 and 2,000 mg per day, which can be administered in a single dose or in the form of individual divided doses from 1-4 times per day.

The compounds of this invention also have useful antifungal activities. For example, they may be used to control strains of *Penicillium sp., Aspergillus niger, Cladosporium sp., Cochliobolus miyabeorus* and *Helminthosporium cynodnotis*. For those utilities they are admixed with suitable formulating agents, powders, emulsifying agents or solvents (such as aqueous ethanol) and sprayed or dusted on the plants to be protected.

In addition, the compounds of the invention may also be useful in elevating HDL-cholesterol levels while lowering levels of LDL-cholesterol and serum triglycerides.

Compounds of formula I can be prepared by the following exemplary process.

Preparation of the compound

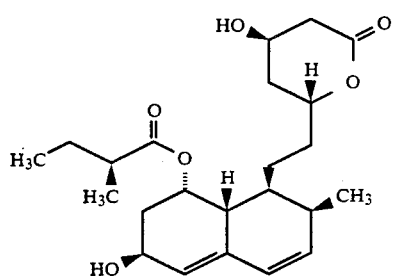

II is described in U.S. Pat. Nos. 3,983,140 and 4,346,227. In the process of forming compound I, compound II is placed in an inert solvent (e.g., tetrahydrofuran or dichloromethane) under an inert atmosphere (e.g., argon or nitrogen) at a temperature of about 15° to 25° C. and treated with an appropriate silyl protecting agent (e.g., t-butyldimethylsilyl chloride, triethylsilyl chloride, or phenyldimethylsilyl chloride) in the presence of an appropriate amine base (e.g., imidazole, dimethylaminopyridine, or diisopropylethylamine) to form

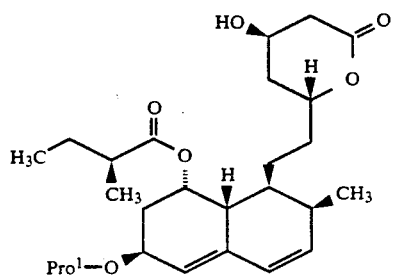

III wherein Pro¹ is a silyl oxygen-protecting group such as

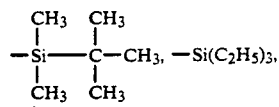

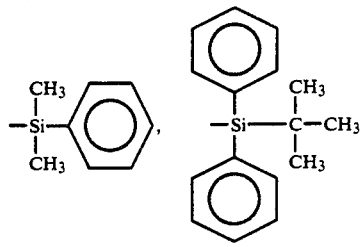

and the like.

Compound III is hydrogenated (e.g., with hydrogen gas) in an organic solvent (e.g., ethyl acetate) in the presence of a catalyst (e.g., platinum on carbon) to form a compound of the formula

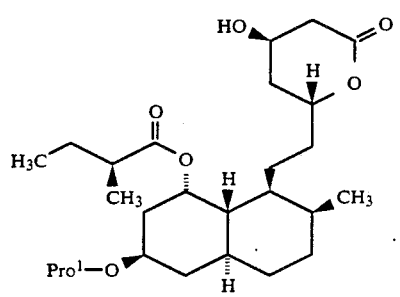

IV

Compound IV is treated with a base (e.g., potassium hydroxide) in a mixture of water and an organic solvent such as toluene (optionally containing some methanol) to form the potassium

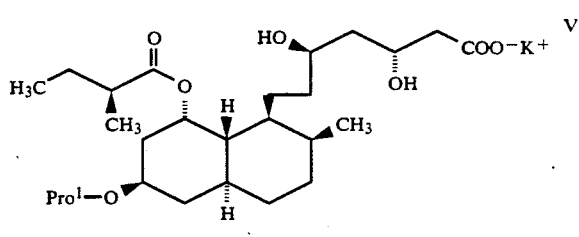

V

The potassium salt V is reacted in an organic solvent such as tetrahydrofuran with an organic base (e.g., pyrrolidine or peperidine) and n-butyllithium and an alkylating agent (e.g., iodomethane) in an inert atmosphere (e.g., argon) at about −60° to −20° C. (See European Patent Application 137,444 A2). The resulting product is acidified, isolated and heated to about 100°–110° C. in an organic solvent (e.g., toluene) to form the lactone

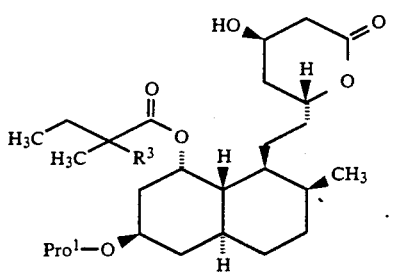

VI

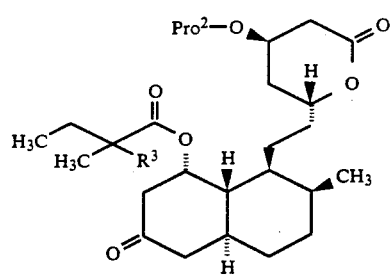

IX

Compound VI is oxygen-protected by, for example, reaction with a protecting agent (e.g., benzyl bromonethyl ether or 4-methoxybenzyl bromomethyl ether) in the presence of an amine base (e.g., N,N-diemthylaniline) in an organic solvent (e.g., methylene chloride) to form Reaction of compounds VIII or IX with a fluorinating agent such as dimethylaminosulfur trifluoride, morpholinosulfur trifluoride, or diethylaminosulfur trifluoride (which is preferred) forms the product

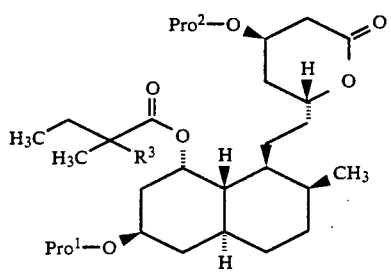

VII

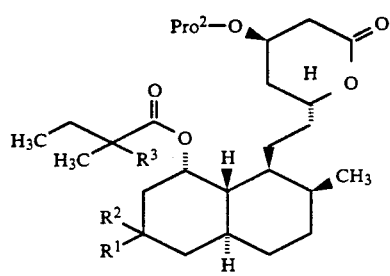

X wherein $Pro^2$ is a different protecting group from $Pro^1$ and may be selected from benzyloxymethyl (which is preferred), paramethoxybenzyloxymethyl, tetrahydrylpyranyloxy, lower acyl and the like.

$Pro^1$ can then be removed by, for example, reaction with a deprotecting agent (e.g., hydrogen fluoride-pyridine) at about $-10°$ to $10°$ C. under an inert atmosphere (e.g., nitrogen) in an inert solvent (e.g., acetonitrile) to form and, when compound IX is used, the additional side product

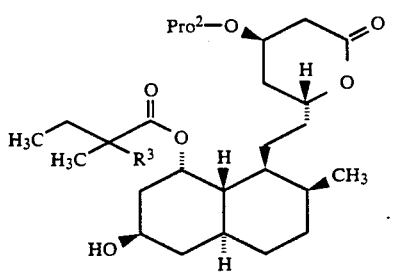

VIII

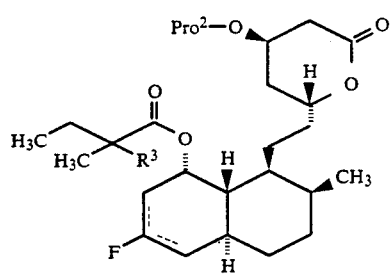

XI

Alternatively, to form Compound I wherein $R^3$ is hydrogen, Compound III is (1) placed in a degassed suspension of a metal catalyst (e.g., platinum on carbon) in an inert organic solvent (e.g., ethyl acetate or tetrahydrofuran), (2) subjected to hydrogen gas under a pressure of about 30 to 60 psi, and (3) oxygen-protected as described above (Compound VI→Compound VII) to form Compound VII wherein $R^3$ is hydrogen. Compound VII is also oxygen-deprotected as described above (Compound VII→Compound VIII) to give compound VIII wherein $R^3$ is hydrogen.

Compound VIII may be treated with an oxidizing agent (Dess Martin periodinane preferred) to form th corresponding 6-ketone Compounds X and XI then undergo catalytic hydrogenolysis (e.g., with palladium on activated carbon) to form compound I wherein Z is in the lactone form

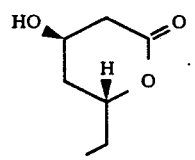

Under these conditions, compound XI forms the compound of formula I having the more specific formula

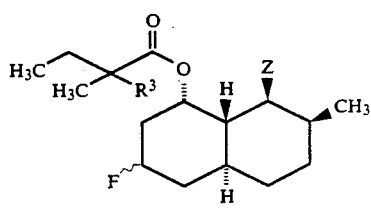

IA wherein Z is in the lactone form. To form the compound of formula I having the more specific formula

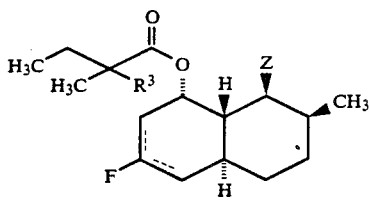

IB wherein Z is in the lactone form, compound XI is deprotected with an oxidizing agent (e.g., 2,3-dichloro-5,6-dicyano-1,4-benzoquinone in moist dichloromethane). Compound I in lactone form may be converted to the open-chain form wherein Z is

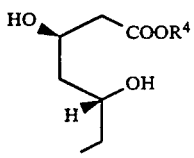

by reaction with an aqueous ammonium or alkali metal base (e.g., lithium hydroxide) at about 20° to 30° C. in an inert solvent (e.g., tetrahydrofuran). $R^4$ can be converted to hydrogen by treatment with a mild aqueous acid (e.g., potassium bisulfate).

The following working examples represent preferred embodiments of the invention. Unless otherwise specified, all temperatures are in degrees Celsius (°C). The preparation of each compound appears below its name. As a shorthand reference, the compound prepared in part 1-A will be called "compound 1-A" or "intermediate 1-A" and so forth for all compounds hereafter.

EXAMPLE 1

[1S-[1′,4aα,7β,8β(2S*,4S*),8aβ]]-2-Methylbutanoic acid, 3,3-difluorodecahydro-7-methyl-8-[2-(tetra-hydro-4-hydroxy-6-oxo-2H-pyran-2-yl)ethyl]-1-naphthalenyl ester 1-A.
[1S-[1α(R*),3β,4β,7β,8β(2S*,4S*),8aβ]]-2-Methylbutanoic acid, 3-[[(1,1-dimethyl-ethyl)dimethylsilyl]oxy]-1,2,3,7,8,8a-hexahydro-7-methyl-8-[2-(tetrahydro-4-hydroxy-6-oxo-2H-pyran-2-yl)ethyl]-1-naphthalenyl ester The starting material for preparation of intermediate A was [1S-[1α(R*), 3β, 4β, 7β, 8β(2S*,4S*),8Aβ]]-2-methylbutanoic acid, 3-hydroxy-1,2,3,7,8,8a-hexahydro-7-methyl-8-[2-(tetrahydro-4-hydroxy-6-oxo-2H-pyran-2-yl)ethyle]-1-naphthalenyl ester. Preparation of this starting material has been described in U.S. Pat. Nos. 3,983,140 and 4,346,227.

A solution of 8.43 g (20.7 mmol, 1.00 eq.) of the starting material in 80 ml of dry tetrahydrofuran under argon at ambient temperature was treated with 1.76 g (25.9 mmol, 1.25 eq.) of imidazole, followed by 3.44 g (22.8 mmol, 1.10 eq.) of t-butyldimethylsilyl chloride. A white precipitate forms almost immediately (5–10 sec). After stirring for 26 hours, the reaction mixture was diluted with 80 ml of ether, filtered and concentrated in vacuo. Purification of the residue by flash chromatography (with Merck silica gel; 40% ethyl acetate in hexanes) gave 7.41 g (a 69% yield) of the mono-silylated product (intermediate A) as a white solid, with a melting point of 111° to 115° C. Lowering the temperature of the reaction or slowly adding a solution of the t-Butyldimethyl silyl chloride in tetrahydrofuran may improve the yield somewhat.

1-B. [1S-[1α(R*),3β,4aβ,7β,8β(2S*,4S*), 8aβ]]-2-Methylbutanoic acid, 3-[[(1,1-dimethylethyl) -dimethylsilyl]oxy]decahydro-7-methyl-8-[2-(tetrahydro-4-hydroxy-6-oxo-2H -pyran-2-yl)-ethyl]-1-naphthalenyl ester To a degassed, argon-purged solution of 9.38 g (18.0 mmol) of intermediate 1-A in 200 ml of ethyl acetate was added 1.4 g of 10% platinum on carbon. This suspension was subjected to 50 psi of $H_2$ in a Parr hydrogenation apparatus for 14.5 hours. Thin layer chromatography analysis indicated the complete consumption of intermediate 1-A with generation of intermediate 1-B and a by-product. The filtered reaction mixture was concentrated, and the products were isolated by flash chromatography. Elution with 45% hexanes in ethyl acetate gave 7.73 g (82%) of intermediate B as a clear glass and elution with 30% hexanes in ethyl acetate gave 0.98 g (13%) of desilylated product.

1-C.
[1S-[1α(R*),3β,4aβ,7β,8β(2S*,4S*),8aβ]]-2-Methylbutanoic acid, 3-[[(1,1-dimethylethyl)-dimethylsilyl]oxy]decahydro-7-methyl-8-[2-[tetrahydro-6-oxo-4-[(phenylmethoxy)methoxy]-2H-pyran-2-yl]ethyl]-1-naphthalenyl ester Generation of benzyloxymethyl bromide was carried out by bubbling hydrobromide through a methylene chloride solution of benzyloxymethyl chloride for 15 minutes at 0° C., followed by stirring at ambient temperature for 45 minutes and exhaustively stripping in vacuo all volatiles. It can also be prepared by reacting equimolecular amounts of benzyl alcohol and paraformaldehyde with hydrogen bromide gas in dichloroform at about 0° C. in the presence of a dehydrating agent such as anhydrous magnesium sulfate, filtering the mixture, and evaporating to remove the solvent.

To a solution of 23.1 g (115 mmol, 2.42 eq) of benzyloxymethyl bromide in 40 ml of methylene chloride at 0° C. was added 15.6 ml (123 mmol, 2.60 eq) of N,N-dimethylaniline and a solution of 24.9 g (47.4 mmol, 1.0 eq) of intermediate 1-B in 50 ml of methylene chloride. This mixture was brought immediately to ambient temperature and stirred for 18 hours. The reaction mixture was then diluted with 400 ml of ethyl acetate, washed sequentially with saturated aqueous copper sulfate (1×200 ml, 1×75 ml) and brine (1×150 ml), dried with magnesium sulfate and concentrated. The product was isolated by elution from silica gel with 10% ethyl acetate in hexanes, yielding 29.4 g (96.1%) of intermediate 1-C as a clear, colorless, viscous oil.

1-D. [1S-[1α(R*),3β,4aα,7β,8β(2S*,4S*), 8aβ]]-2-Methylbutanoic acid, 3-hydroxydecahydro-7-methyl-8-[2-[tetrahydro-6-oxo-4-[(phenylmethoxy)methoxy]-2H-pyran-2-yl]ethyl]-1-naphthalenyl ester A solution of 28.8 g (44.7 mmol) of intermediate 1-C in 400 ml of acetonitrile was cooled at −20° C. under argon and treated with three 10 ml portions of HF-pyridine over 2 hours, with warming to 0° C. after 1.5 hours.

The reaction mixture was diluted with 500 ml of ethyl acetate and washed sequentially with saturated copper sulfate (aqueous, 2×150 ml), brine (1×250, 200 and 150 ml) and saturated sodium bicarbonate (aqueous 2×250 ml, 1×200 ml). After drying the ethyl acetate solution with sodium sulfate and concentrating, the crude product was purified by silica gel chromatography, eluting with 40% hexanes in ethyl acetate to yield 2.2 g (93.7%) of intermediate 1-D as a clear, colorless oil.

1-E. [1S-[1α(R*),3β,4aα,7β,8β(2S*,4S*), 8aβ]]-2-Methylbutanoic acid, 7-methyldecahydro-3-oxo-8-[2-[tetrahydro-6-oxo-4-[(phenylmethoxy)methoxy]-2H-pyran-2-yl]ethyl]-1-naphthalenyl ester To a stirred suspension of Dess-Martin periodinane (264 mg, 0.622 mmol) in dichloromethane (2 ml) at room temperature under an atmosphere of nitrogen was added dropwise a solution of compound 1-D (300 mg, 0.565 mmol) in dichloromethane (3 ml) followed by t-butyl alcohol (59 μl, 0.622 mmol). After 1.5 hours, the mixture was poured into a stirred mixture of sodium bicarbonate (240 mg) in 0.5 M sodium thiosulfate (5 ml) and dichloromethane (25 ml). The mixture was stirred vigorously until the two layers were clear. The dichloromethane layer was separated, washed with brine, dried over anhydrous sodium sulfate and evaporated in vacuo to give a gum. This gum was flash-chromatographed on a column of silica gel (20 g, LPS-1), eluting with ethyl acetate-hexane (3:7) to give 275 mg (92.1%) of thin layer chromatography (TLC) homogeneous compound 1-E as a gum with consistent $H^1$-NMR and $C^{13}$-NMR spectra. Another run using 850 mg of compound 1-D gave 780 mg more of compound 1-E.

1-F. [1S-[1α(R*),3β,4aα,7β,8β(2S*,4S*), 8aβ]]-2-Methylbutanoic acid, 3,3-difluorodecahydro-7-methyl-8-[2-[tetrahydro-6-oxo-4-[(phenylmethoxy)methoxy]-2H-pyran-2-yl]ethyl]-1-naphthalenyl ester To a chilled (−45°, Dry ice-acetonitrile bath) and stirred solution of diethylaminosulfur trifuoride (DAST, 183 mg, 1.135 mmol) in dichloromethane (1 ml) under an atmosphere of nitrogen was added dropwise a solution of compound 1-E (100 mg, 0.189 mmol) in dichloromethane (1 ml). After the addition was complete, the solution was gradually warmed up to room temperature and stirred overnight (20 hours). The resulting solution was cooled to 0° (ice bath), quenched with a solution of sodium acetate (61 mg in 1.0 ml of water), stirred for 20 minutes, diluted with brine (5 ml) and extracted with dichloromethane (3×5 ml). The combined dichloromethane extracts were washed with brine, dried over anhydrous sodium sulfate and evaporated in vacuo to give a gum. This gum was flash-chromatographed on a column of silica gel (20 g, LPS-1), eluting successively with ethyl acetate-hexane (15:85, 30:70 and 50:50) to give 35 mg (33.3%) of compound 1-F as a gum with consistent $H^1$-NMR and spectra, and other products. Another run using 865 mg of compound 1-E gave 300 mg more of compound 1-F.

1-G. 1S-[1α,4aα,7β,8β(2S*,4S*), 8aβ]]-2-Methyl-butanoic acid, 3,3-difluorodecahydro-7-methyl-8-[2-(tetrahydro-4-hydroxy-6-oxo-2H-pyran-2-yl)ethyl]-1-naphthalenyl ester A solution of compound 1-F (100 mg, 0.182 mmol) in ethyl acetate (5 ml) containing 20% palladium hydroxide on carbon (85 mg) was hydrogenated at atmospheric pressure at room temperature for 6.5 hours. It was then filtered through a bed of Celite ® and washed with a small amount of ethyl acetate. The filtrate and washings were combined and evaporated in vacuo to give a gum. This gum was chromatographed on a column of silica gel (15 g, Baker 60–200 mesh), eluting with ethyl acetate-dichloromethane (2:8) to give 73 mg (93%) of compound 1-G (Example 1) as a solid, m.p. 161°–163°, with consistent $H^1$-NMR and $C^{13}$-NMR spectra. Another run using 220 mg of compound 1-F gave 160 mg more of compound 1-G.

EXAMPLE 2

[1S-[1α(αS*,ΔS*),2α,4aβ,8aα]]-6,6-Difluorodecahydro-β, Δ-dihydroxy-2-methyl-8-(2-methyl-1-oxobutoxy)-1-naphthaleneheptanoic acid, monolithium salt A stirred solution of Compound 1-G (200 mg, 0.465 mmol) in tetrahydrofuran (8 ml) at room temperature under an atmosphere of nitrogen was treated with 1.0 N lithium hydroxide (1.39 ml, 1.393 mmol). After 15 minutes, the solvent was evaporated by a stream of nitrogen to give a gum. This gum was dissolved in water and chromatographed on a column of HP-20 (1.5"×1" column bed), eluting with deionized, distilled water (about 250 ml) and 50% methanol-water (about 250 ml) to give in the later eluate TLC-homogeneous Example 2. This eluate was evaporated in vacuo and lyophilized overnight to give 150 mg (71%) of a hydrated analytical specimen of Example 2 as a white solid with consistent IR, mass and $H^1$-NMR spectral data.

Anal. Calc'd for $C_{23}H_{37}F_2O_6Li \cdot 0.2H_2O$ (MW: 454.45 ±0.2 $H_2O$):

Calc'd: C,60.30; H,8.23; F,8.29.

Found: C,60.31; H,8.33; F,8.14.

IR Spectrum (KBr):

3421 cm$^{-1}$(OH), 1727 cm$^{-1}$(C=O,ester), 1583 cm$^{-1}$(C=O,acid salt).

Mass spectrum: (M-H)$^-$=447, (M+Li)$^+$=455, (M+Li-2H)$^-$=453, (M+2Li-H)$^+$=461, (M+3Li-2H)$^+$=467, etc.

H1-NMR Spectrum of Example 2 ($D_2O$,270 MHz): δ0.75(d,3H,J=~8.0,CH$_3$), 0.80(t,3H,J=~8.0,CH$_3$), 1.80(d,3H,J=~8.0,CH$_3$), 3.65(d,J=~6.6,1H,CHOH), 4.03(quintlet,J=~5.9,5.5,1H,CH-OH), 5.19(s,1H,CH-O)ppm.

EXAMPLE 3

1S-[1α(R*),3α,4aα,7β,8β(2S*,4S*), 8aβ]]-2-Methyl-butanoic acid, 3-fluorodecahydro-7-methyl-8-[2-tetrahydro-6-oxo-4-hydroxy-2H-pyran-2-yl]ethyl]-naphthalenyl ester

3-A.

[1S-[1α(R*),3α,4aα,7β,8β(2S*,4S*),8aβ]]-2-Methyl-butanoic acid, decahydro-3-fluoro-7-methyl-8-[2-[tetrahydro-6-oxo-4-[(phenylmethoxy)me-2H-pyran-2-yl]ethyl]-1-naphthalenyl ester To a chilled (−40°, Dry ice-acetonitrile bath) and stirred suspension of dimethylaminosulfur trifluoride (DAST, 1.13 g, 8.48 mmol) and pre-dried cesium fluoride (1.29 g, 8.48 mmol) in dry tetrahydrofuran (10 ml) under an atmosphere of nitrogen was added dropwise a solution of compound 1-D (1.5 g, 2.83 mmol) in dry tetrahydrofuran (10 ml). After 3.5 hours at −40°, the mixture was gradually warmed up to room temperature, stirred for 40 hours, cooled to 0° C. (ice bath), quenched with sodium acetate (2 g in 5 ml of water), diluted with brine (20 ml) and extracted with dichloromethane (3×20 ml). The combined dichloromethane extracts were washed with brine, dried over anhydrous sodium sulfate and evaporated in vacuo to give a gum. This gum was flash-chromatographed on a column of silica gel (200 g, LPS-1), eluting successively with ethyl acetate-hexane (1:4, 3:7 and 1:1) to give 140 mg (9.3%) of compound 3-A as a gum with consistent $H^1$-NMR and spectra, and other products. Another run using 100 mg of compound 1-D reacted with diethylaminosulfur trifluoride in dichloromethane without cesium fluoride, gave 16 mg more of compound 3-A.

3-B. [1S-[1α(R*),3α,4aα,7β,8β(2S*,4S*), 8aβ]]-2-Methylbutanoic acid, 3-fluorodecahydro-7-methyl-8-[2-[tetrahydro-6-oxo-4-hydroxy-2H-pyran-2-yl]ethyl]-1-naphthalenyl ester A slow stream of hydrogen was bubbled through a suspension of compound 3-A (25 mg, 0.047 mmol) in ethyl acetate (3 ml) containing 20% palladium hydroxide on carbon (18 mg) at room temperature for 1 hour. It was then filtered through a bed of Celite® and washed with a small amount of ethyl acetate. The filtrate and washings were combined and evaporated in vacuo to give a gum. This gum was chromatographed on a column of silica gel (10 g, Baker 60-200 mesh), eluting with ethyl acetate-dichloromethane (1:4) to give 17 mg (77.4%) of TLC-homogeneous compound 3-B as a gum with consistent $H^1$-NMR and $C^{13}$-NMR spectra. Another run using 110 mg of compound 3-A gave 78 mg more of compound 3-B (Example 3).

$H^1$-NMR Spectrum (CDCl$_3$, 270 MHz): δ0.85 (d,3H,J=8.0,CH$_3$), 0.90 (t,3H,J=8.0,CH$_3$) 2.65 (m,2H,CH$_2$C=0), 4.35 (S,1H,C$\underline{H}$—OH), 4.58 (broad,S,1H,C$\underline{H}$—0), 4.83 (d,1H,H=52 Hz,C$\underline{H}$—F), $C^{13}$-NMR Spectrum (CDCl$_3$,270 MHz): δ 176.5, 170.35, 88.96, 86.46, 62.63, 43.00, 41.76, 39.50, 38.61, 38.39, 38.05, 36.18, 34.64, 33.12, 32.45, 30.35, 28.85, 27.62, 26.47, 24.55, 16.68 and 11.71 ppm.

EXAMPLE 4

[1S-[1α(βS*,ΔS*),2α,4aβ,6β,8β(R*),8aα]]-6-Fluorodecahydro-β, Δ-dihydroxy-2-methyl-8-(2-methyl-1-oxobutoxy)-1-naphthaleneheptanoic acid, monolithium salt A stirred solution of Compound 3-B (110 mg, 0.267 mmol) in tetrahydrofuran (3 ml) at room temperature under an atmosphere of nitrogen was treated with 1.0 N lithium hydroxide (799 µl, 0.799 mmol). After 1 hour, the solvent was evaporated by a stream of nitrogen to give a gum. This gum was dissolved in water and chromatographed on a column of HP-20 (1"×1" column bed), eluting with deionized, distilled water (about 250 ml) to give in the later eluate TLC-homogeneous Example 4. This eluate was evaporated in vacuo and lyophilized overnight to give 80 mg (68.7%) of a hydrated analytical specimen of Example 4 as a white solid with consistent IR, mass and $H^1$-NMR spectra.

Anal. Calc'd for $C_{23}H_{38}FO_6Li.0.5 H_2O$ (MW=436.50+0.5 H$_2$O):

Calc'd: C,62.00; H,8.82; F,4.26.
Found: C,62.05; H,8.82; F,3.66.

IR Spectrum (KBr):
3414 cm$^{-1}$ (OH), 1725 cm$^{-1}$ (C=O,ester),
1584 cm$^{-1}$ (C=0 acid salt).

Mass spectrum:
$(M-H)^{31}$=429,$(M+H)^+$=437,$(M+2Li)^-$=443, etc.

$H^1$-NMR Spectrum of Example 4 (D$_2$O, 270 MHz): δ 0.77 (d,3H,J=~8.0,CH$_3$), 0.83 (t,3H,J=~8.0,CH$_3$), 1.05 (d,3H,J=~8.0,CH$_3$), 3.65 (M,1H,C$\underline{H}$—OH), 4.02 (quintlet, 1H,H$_6$') 4.93 (d,1H,J=47.5,C$\underline{H}$—F) 5.07 (S,1H,C$\underline{H}$—O)ppm.

EXAMPLE 5

1S-[1α(R*),3β,4aα,7β,8β(2S*,4S*), 8aβ]]-2-Methylbutanoic acid, 3-fluorodecahydro-7-methyl-8-[2-tetrahydro-6-oxo-4-hydroxy-2H-pyran-2-yl]ethyl]-1-naphthalenyl ester

5-A.

[1S-[1α(R*),3β,4aα,7β,8β(2S*,4S*),8aβ]]-2-Methyl-butanoic acid, 3-fluorodecahydro-7-methyl-8-[2-[tetrahydro-6-oxo-4-[(phenylmethoxy) methoxy]-2H-pyran-2-yl]ethyl]-1-naphthalenyl ester To a chilled (ice bath) and stirred solution of diethylaminosulfur trifluoride (380 mg, 2.36 mmol) in dry dichloromethane (5 mL) under an atmosphere of nitrogen was added a solution of compound 1-D (1.0 g, 1.88 mmol) in dry dichloromethane (5 mL). The solution was then warmed up to room temperature, stirred for 20 hours, quenched with sodium acetate (1.0 g in 5 mL of water), diluted with brine (25 mL) and extracted with dichloromethane (3×25 mL). The combined dichloromethane extracts were washed with brine, dried over anhydrous sodium sulfate and evaporated in vacuo to give a gum. This gum was flash-chromatographed on a column of silica gel (LPS-1, 200 g), eluting successively with ethyl acetate-hexanes (15:85, 20:80 and 30:70) to give 400 mg (39.9%) of Compound 5-A, as a gum, with consistent $^1$H-NMR and $^{13}$C-NMR spectra, and other products.

5-B. [1S-[1α(R*),3β,4aα,7β,8β(2S*,4S*), 8aβ]]-2-Methylbutanoic acid, 3-fluorodecahydro-7-methyl-8-2-[tetrahydro-6-oxo-4-hydroxy-2H-pyran-2-yl]ethyl]-1-naphthalenyl ester A slow stream of hydrogen was bubbled through a suspension of Compound 5-A (150 mg, 0.282 mmol) in ethyl acetate (5 mL) containing 20% palladium hydroxide on carbon (70 mg) at room temperature for 2 hours. The mixture was then filtered through a bed of Celite ® and washed with a small amount of ethyl acetate. The filtrate and washings were combined and evaporated in vacuo to give a gum. This gum was chromatographed on a column of silica gel (LPS-1, 50 g), eluting with ethyl acetate-dichloromethane (1:9) to give 85 mg (96.9%) of Compound 5-A as a gum with consistent $^1$HNMR and $^{13}$C-NMR spectra. Another run using 190 mg of Compound 5-A gave 115 mg more of Compound 5-B (Example 5). H$^1$-NMR Spectrum (CDCl$_3$, 270 MHz): δ 0.82 (d,3H,J=8.0,C$\underline{H}_3$), 0.90 (t,3H,J=8.0,C$\underline{H}_3$), 1-15 (d,3H,J=8.0,C$\underline{H}_3$), 2.65 (m,2H,CH$_2$C=0), 3.20 (S,1H,CH—O$\underline{H}$), 4.32 (S,1H,C$\underline{H}$—OH), 4.60 (broad, 1H,C$\underline{H}$—O), 4.67 (m,1H,J=~52,C$\underline{H}$—F), 5.33 (S,1H, C$\underline{H}$—O)ppm.

C$^{13}$-NMR Spectrum (CDCl$_3$, 270 MHz): 175.9, 170.7, 89.73, 87.22, 69.90, 62.29, 42.91, 41.53, 41.40, 39.91, 39.68, 39.65, 38.50, 37.23, 36.96, 35.85, 35.07, 34.90, 32.86, 32.65, 28.62, 27.79, 26.66, 26.55, 26.56, 16.67, 11.63, 11.65 ppm.

EXAMPLE 6

[1S-[1α(βS*,ΔS*),2α,4aβ,6α,8β(R*),8aα]]-6-Fluorodecahydro-β, Δ-dihydroxy-2-methyl-8-(2-methyl-1-oxobutoxy)-1-naphthaleneheptanoic acid, monolithium salt A stirred solution of Compound 5-B (125 mg, 0.303 mmol) in tetrahydrofuran (3 mL), at room temperature under an atmosphere of nitrogen was treated with 1.0 N lithium hydroxide (606 μL, 0.606 mL). After 30 minutes, the solvent was mostly evaporated under a stream of nitrogen to leave a gummy residue. This residue was dissolved in water and chromatographed on a column of HP-20 (1"×1.5" column bed), eluting with deionized, distilled water (about v250 mL) and 50% methanol-water (about 250 mL) to give in the later eluate TLC-homogeneous Example 6. This eluate was evaporated in vacuo and lyophilized overnight to give 105 mg (78.9%) of a hydrated analytical specimen of Example 6 as a white solid with consistent IR, mass and $^1$HNMR spectra.

Anal. calc'd for C$_{23}$H$_{38}$FO$_6$Li.0.3 H$_2$O (MW=441.90):

C,62.52; H,8.80; F,4.30.

Found: C,62.78; H,9.34; F,4.32.

IR Spectrum (KBr): 3432 cm (OH), 1728 cm (C=O,ester), 1584 cm$^{-1}$ (C=O,acid salt).

Mass Spectrum: (M+H)$^+$=437 (Salt), (M−H)$^-$=429 (acid).

$^1$HNMR Spectrum of Example 6 (D$_2$O, 270 MHz): δ 0.74 (d,3H,J=7.03,CH$_3$), 0.83 (t,3H,J=7.6,CH$_3$), 1.09 (d,3H,J=7.03,CH$_3$), 3.63 (m,1H,J=5.8,C$\underline{H}$—OH), 4.03 (quintlet,1H,J=7.0,5.7,C$\underline{H}$—OH), 4.65 and 4.83 (2 m,1H,CH—F), 5.23 (s,1H,,C$\underline{H}$—O)ppm.

EXAMPLE 7

[1S-[1α(R*),3β,4aα,7β,8β(2S*,4S*),8aβ]]-2,2-Dimethylbutanoic acid 3-fluorodecahydro-7-methyl-8-[2-(tetrahydro-4-hydroxy-6-oxo-2H-pyran-2-yl)-ethyl]-1-naphthalenyl ester

7-A.

[1S-[1α(R*),3β,4aα,7β,8β(2S*,4S*),8aβ]]-2-Methylbutanoic acid, 3-[[(1,1-dimethylethyl)dimethylsilyl]oxy]decahydro-7-methyl-8-[2-(tetrahydro-4-hydroxy-6-oxo-2H-pyran-2-yl)ethyl]-1-naphthalenyl ester To a degassed, argon-purged solution of 9.38 g (18.0 mmol) of Compound 1-A in 200 mL of ethyl acetate was added 1.4 g of 10% platinum on carbon. This suspension was subjected to 50 psi of H$_2$ in a consumption of starting material with generation of the desired product and some desilylated product. The filtered reaction mixture was concentrated and the products were isolated by flash chromatography. Elution with 45% hexanes in ethyl acetate gave 7.73 g (82%) of compound 7-A as a clear glass and elution with 30% hexanes in ethyl acetate gave 0.98 g (13%) of desilylated product.

7-B.

[1S-[1α(R*),3β,4aα,7β,8β(2S*,4S*),8aβ]]-2,2-Dimethylbutanoic acid,3-[[(1,1-dimethylethyl)dimethylsilyl]oxy]decahydro-7-methyl-8-[2-(tetrahydro-4-hydroxy-6-oxo-2H-pyran-2-yl)ethyl]-1-naphthalenyl ester A solution of compound 7-A (10.5 g, 20.04 mmol) in a mixture of toluene (200 mL) and methanol (42 mL) was treated with 1.0 N potassium hydroxide (20 mL) at room temperature under an atmosphere of nitrogen for 45 minutes. The solvent was evaporated in vacuo to give a gum. This gum was azeotroped with benzene (250 mL) and then dried in vacuo at 45° (oil bath temperature) overnight to give a foamy solid.

To a chilled (−55°, acetonitrile-Dry ice bath) and stirred solution of the above solid in dry tetrahydrofuran (150 mL) under an atmosphere of nitrogen was added dry pyrrolidine (6.48 mL, 77.63 mmol), followed by n-butyllithium (2.5 M in hexane, 27.84 mL, 69.6 mmol). The mixture was gradually warmed up to −25° (carbon tetrachloride-Dry ice bath) and stirred for 2.5 hours. Iodomethane (3.12 mL, 50.12 mmol) was added dropwise. After 1.0 hour, a small aliquot was worked up. $^1$H-NMR spectrum indicated there was 15-20% non-methylated starting material present.

Therefore, the mixture was recooled to −55°, more dry pyrrolidine (3.24 mL) and n-butyllithium (2.5 M in hexane, 13.92 mL) were added, and the mixture was warmed up to −25°. After 2.5 hours, iodomethane (1.56 mL) was added and the mixture was stirred for another hour. The resulting mixture was quenched with 10% potassium bisulfate solution (100 mL) at −25°, warmed up to room temperature, saturated with sodium chloride and extracted with ethyl acetate (3×100 mL). The combined ethyl acetate extracts were washed with a small amount of 5% sodium and brine, dried over anhydrous sodium sulfate and evaporated in vacuo to give a gummy residue (11.0 g).

The above gum was refluxed in dry toluene (200 mL) under an atmosphere of nitrogen for 4.0 hours. The solvent was then evaportated in vacuo to give a gummy material. This gum was chromatographed on a column of silica gel (LPS-1, 450 g), eluting with ethyl acetate-hexane (1:3) to give 7.3 g (67.5) of Compound 7-B as a gum with consistent $^1$HNMR and $^{13}$C-NMR spectra.

7-C.

[1S-[1α(R*),3β,4aα,7β,8β(2S*,4S*),8aβ]]-2,2-Dimethylbutanoic acid,3-[[(1,1-dimethylethyl)dimethylsilyl]oxy]decahydro-7-methyl-8-[2-[tetrahydro-4-[(phenylmethoxy)methoxy]-6-oxo-2H-pyran-2-yl]-ethyl]-1-naphthalenyl ester To a chilled (0°, ice bath) and stirred solution of Compound 7-B (7.3 g, 13.52 mmol) in dry dichloromethane (80 mL) under an atmosphere of nitrogen was added dry N,N-dimethylaniline (3.7 g, 30.53 mmol). After 15 minutes, benzyl bromomethyl ether (5.62 g, 26.13 mmol) was added. The resulting solution was gradually warmed up to room temperature and stirred for 20 hours. The solvent was partially removed in vacuo. Ethyl acetate (300 mL) was added. The ethyl acetate solution was washed with a 10% potassium bisulfate solution, a saturated sodium bicarbonate solution and brine, dried over anhydrous sodium sulfate and evaporated in vacuo to give an oil. This oil was chromatographed on a column of silica gel (LPS-1, 300 g), eluting with ethyl acetate-hexane (1:9) to give 8.5 g (95.4%) of Compound 7-C as an oil with consistent $^1$HNMR and $^{13}$C-NMR spectra.

[1S-[1α(R*),3β,4aα,7β,8β(2S*,4S*),8aβ]]-2,2-Dimethylbutanoic acid, 3-hydroxydecahydro-7-methyl-8-[2-[tetrahydro-4-[(phenylmethoxy)methoxy]-6-oxo-2H-pyran-2-yl]-ethyl]-1-naphthalenyl ester A solution of Compound 7-C (8.5 g, 12.9 mmol) in dry acetonitrile (100 mL) was cooled to 0° (ice bath) under an atmosphere of nitrogen and treated with two 4 mL portions of hydrogen fluoride-pyridine over 1.5 hours. The reaction mixture was diluted with ethyl acetate (200 mL), washed with a 10% potassium hydrogen sulfate solution, brine and a dilute sodium bicarbonate solution, dried over anhydrous sodium sulfate and evaporated in vacuo to give a gum. This gum was chromatographed on a column of silica gel (Baker 60-200 mesh, 300 g), eluting with ethyl acetate-hexane (35:65 and 1:1) to give 6.0 g (85.4%) of Compound 7-D as a solid (m.p 73°-77°) with consistent $^1$HNMR and $^{13}$C-NMR spectra.

7-E.

[1S-[1α(R*),3β,4aα,7β,8β(2S*,4S*),8aβ]]-2,2-Dimethylbutanoic acid, 3-fluorodecahydro-7-methyl-8-[2-[tetrahydro-4-[(phenylmethoxy)methoxy]-6-oxo-2H-pyran-2-yl]-ethyl]-1-naphthalenyl ester To a chilled (ice bath) and stirred solution of diethylaminosulfur trifluoride (302 mg, 1.88 mmol) in dry dichloromethane (5 mL) under an atmosphere of nitrogen was added a solution of Compound 7-D (815 mg, 1.5 mmol) in dry dichloromethane (5 mL). The solution was then warmed up to room temperature, stirred for 20 hours, quenched with sodium acetate (0.8 g in 3 mL of water), diluted with brine (25 mL) and extracted with dichloromethane (3×25 mL). The combined dichloromethane extracts were washed with brine, dried over anhydrous sodium sulfate and evaporated in vacuo to give a gum. This gum was flash-chromatographed on a column of silica gel (LPS-1, 200 g), eluting successively with ethyl acetate-hexane (15:85, 20:80 and 30:70) to give mg (40.3%) of Compound 7-E as a gum with consistent $^1$HNMR and $^{13}$C-NMR spectra.

7-F.

[1S-1α(R*),3β,4aα,7β,8β(2S*,4S*),8aβ]]-2,2-Dimethylbutanoic acid, 3-fluorodecahydro-7-methyl-8-[2-(tetrahydro-4-hydroxy-6-oxo-2H-pyran-2-yl)ethyl]-1-naphthalenyl ester A slow stream of hydrogen was bubbled through a suspension of Compound 7-E (330 mg, 0.604 mmol) in ethyl acetate (7 mL) containing 20% palladium hydroxide on carbon (150 mg) at room temperature for 5 hours. The reaction mixture was then filtered through a bed of Celite ® and washed with a small amount of ethyl acetate. The filtrate and washings were combined and evaporated in vacuo to give a gum. This gum was chromatographed on a column of silica gel (LPS-1, g), eluting with ethyl acetate-dichloromethane (1:9) to give 210 mg (80.6%) of Compound 7-F (Example 7) as a gum with consistent $^1$HNMR and $^{13}$C-NMR spectra.

H$^1$-NMR Spectrum (CDCl$_3$, 270 MHz): δ 0.81 (d,3H,J=8.0,CH$_3$), 0.83 (t,3H,J=8.0,CH$_3$),1.13 (S,6H,CH$_3$), 2.36 (m,1H,CH), 2.65 (m,1H,$\overline{\text{CH}}_2$C=0), 4.34 (S,1$\overline{\text{H}}$,CH—OH), 4.58 (broad S,1H,CH—O), 4.68 (m,1H,J=~57, C$\underline{\text{H}}$—F), 5.31 (S,1H, C$\underline{\text{H}}$—O),ppm.

C$^{13}$-NMR Spectrum (CDCl$_3$, 270 MHz): δ 177.3, 170.8, 89.9, 87.4, 76.67, 70.1, 69.9, 62.5, 43.14, 40.1, 39.74, 38.65, 37.35, 37.10, 36.00, 35.36, 35.22, 33.23, 33.03, 32.63, 28.77, 27.93, 24.85, 24.68, 11.75 and 9.33 ppm.

EXAMPLE 8

1S-[1α(βS*,ΔS*),2α,4aβ,6α,8β,8aβ]]-8-(2,2-Dimethyl-1-oxobutoxy)-6-fluorodecahydro-β, Δ-dihydroxy-2-methyl-1-naphthaleneheptanoic acid, monolithium salt A stirred solution of Example 7 (200 mg, 0.469 mmol) in tetrahydrofuran (4 mL) at room temperature under an atmosphere of nitrogen was treated with 1.0 N lithium hydroxide (938 μL, 0.938 mmol). After 30 minutes, the solvent was mostly evaporated by a stream of nitrogen to leave a gummy residue. This residue was dissolved in water and chromatographed on a column of HP-20 (1.5"×1" column bed), eluting with deionized distilled water (about 250 mL) to give in the later eluate TLC-homogeneous Example 8. This eluate was evaporated in vacuo and lyophilized overnight to give 165 mg (78.1%) of a hydrated analytical specimen of Example 8 as a white solid with consistent IR, mass and $^1$HNMR and $^{13}$C-NMR spectra.

Anal. calc'd for C$_{24}$H$_{40}$FO$_6$Li.0.52 H$_2$O (MW=459.89): C,62.68; H,8.99; F,4.13. Found: C,62.68; H,9.36; F,4.07.

IR Spectrum (KBr): 3432 cm$^{-1}$(OH), 1724 cm$^{-1}$(C=O,ester), 1582 cm$^{-1}$(C=O, acid salt).

Mass Spectrum: (M−H)$^-$=443, (M=Li)$^+$=451, (M+Li−2H)$^-$=449, (M+2Li−H)$^+$=457 (M+3Li−2H)$^+$=463, (M+4Li−3H)$^+$=469.

$^1$HNMR spectrum (D$_2$O, 270 MHz): δ0.78 (d+t, 6H, CH$_3$), 1.13 (s, 6H, CH$_3$), 2.25 (m, 2H, C$\underline{\text{H}}_2$C=O), 3.62 (m,1H,C$\underline{\text{H}}$—OH), 4.03 (m, 1H, CH—OH), 4.58 and 4.76 (2 m, 1H, C$\underline{\text{H}}$—F) 5.23 (s, 1H, C$\underline{\text{H}}$—O) ppm.

EXAMPLE 9

[1S-[1α(R*),4aα,7β,8β(2S*,4S*),8aβ]]-2,2-Dimethylbutanoic acid, 3,3-difluorodecahydro-7-methyl-8 [2-(tetrahydro-4-hydroxy-6-oxo-2H-pyran-2yl)-ethyl]-1-naphthalenyl ester

9-A. [1S-[1α(R*),4aα,7β,8β(2S*,4S*), 8aβ]]-2,2-Dimethylbutanoic acid, 7-methyldecahydro-3-oxo-8-[2-(tetrahydro-4-[(phenylmethoxy)methoxy]-6-oxo-2H-pyran-2-yl)ethyl]-1-naphthalenyl ester To a stirred suspension of Dess-Martin periodinane (514 mg, 1.212 mmol) in dichloromethane (5 mL) at room temperature under an atmosphere of nitrogen was added dropwise a soluton of Compound 7-D (600 mg, 1.102 mmol) in dichloromethane (10 mL) followed by t-butyl alcohol (114 μL, 1.212 mmol). After 1.5 hours, the mixture was poured into a stirred mixture of sodium bicarbonate (500 mg) in 0.5 M sodium thiosulfate (10 mL) and dichloromethane (75 mL). The mixture was stirred vigorously until the two layers were clear. The dichloromethane layer was separated, washed with brine, dried over anhydrous sodium sulfate and evaporated in vacuo to give a gum. This gum was flash-chromatographed on a column of silica gel (LPS-1, 40 g), eluting with hyl acetate-hexane (3:7) to give 455 mg (76.1%) of Compound 9-A as a gum with consistent $^1$HNMR and $^{13}$C-NMR spectra.

9-B. [1S-[1α(R*),4aα,7β,8β(2S*,4S*),8aβ]]-2,2-Dimethylbutanoic acid, 3,3-difluorodecahydro-7-methyl-8-[2-[tetrahydro-4-[(phenylmethoxy)methoxy]-6-oxo-2H-pyran-2-yl]ethyl]-1-naphthalenyl ester To a chilled (−40°, acetonitrile-Dry ice bath) and stirred solution of diethylaminosulfur trifluoride (1.6 g, 9.95 mmol) in dichloromethane (6 mL) under an atmosphere of nitrogen was added dropwise a solution of Compound 9-A (900 mg, 1.658 mmol) in dichloromethane (6 mL). After the addition was complete, the solution was gradually warmed up to room temperature and stirred for 20 hours. The resulting solution was cooled to 0° (ice bath), quenched with a solution of sodium acetate (900 mg in 6 mL of water), stirred for 20 minutes, diluted with brine (50 mL) and extracted with dichloromethane (3×50 mL). The combined dichloromethane extracts were washed with brine, dried over anhydrous sodium sulfate and evaporated in vacuo to give a gum. This gum was flash-chromatographed on a column of silica gel (40 g, LPS-1), eluting successively with acetone-hexane (1:9 and 1:4) to give 410 mg (52.8%) of Compound 9-B as a gum with consistent $^1$HNMR and $^{13}$C-NMR spectra.

9-C. [1S-[1α(R*),4aα,7β,8β(2S*,4S*),8aβ]]-2,2-Dimethylbutanoic acid, 3,3-difluorodecahydro-7-methyl-8-[2-(tetrahydro-4-hydroxy-6-oxo-2H-pyran-2-yl)ethyl]-1-naphthalenyl ester A slow stream of hydrogen was bubbled through a suspension of Compound 9-B (400 mg, 0.708 mmol) in ethyl acetate (10 mL) containing 20% palladium hydroxide on carbon (250 mg) at room temperature for 6 hours. The reaction mixture was then filtered through a bed of and washed with a small amount of ethyl acetate. The filtrate and washings were combined and evaporated in vacuo to give a gum. This gum was chromatographed on a column of silica gel (Baker 60–200 mesh, 60 g), eluting with ethyl acetate-dichloromethane (1:9 and 15:85) to give 275 mg (87.3%) of Compound 9-C (Example 9) as a foam with consistent $^1$H-NMR and $^{13}$C-NMR spectra. H$^1$-NMR Spectrum (CDCl$_3$, 270 MHz): δ 0.80 (d,3H,J=7.5,CH$_3$), 0.84 (t,3H,J=7.5,CH$_3$), 1.15 (S,6H,CH$_3$), 2.65 (m,2H,CH$_2$C=O), 4.35 (S,1H,CH—OH), 4.59 (broad S,1H,CH—O) and 5.22 (S,1H,CH—O)ppm. C$^{13}$-NMR Spectrum (CDCl$_3$, 270 MHz): δ 177.56, 170.71, 122.27, 118.73, 76.46, 68.02, 67.85, 62.52, 43.11, 42.56, 41.47, 41.18, 40.81, 39.48, 38.65, 37.95, 37.61, 37.23, 36.08, 33.81, 33.69, 33.03, 32.34, 28.65, 27.39, 24.82, 24.68, 24.48, 11.66 and 9.30 ppm.

EXAMPLE 10

[1S-[1α(βS*,ΔS*),2α,4aβ,8β,8aα]]-8-(2,2-Dimethyl-1-oxobutoxy)-6,6-difluorodecahydro-β,Δ-dihydroxy-2-methyl-1-naphthalene-heptanoic acid, monolithium salt A stirred solution of Compound 9-C (250 mg, 0.563 mmol) in tetrahydrofuran (6 mL) at room temperature under an atmosphere of nitrogen was treated with 1.0 N lithium hydroxide (1.13 mL, 1.13 mmol). After 30 minutes, the solvent was evaporated under a stream of nitrogen to leave a gummy residue. This residue was dissolved in water and chromatographed on a column of HP-20 (2"×1" column bed), eluting with deionized, distilled water (300 mL) and 50% methanol-water (300 mL) to give in the later eluate TLC-homogeneous Example 10. This eluate was evaporated in vacuo and lyophilized overnight to give 190 mg (70.2%) of a hydrated analytical specimen to Example 10 as a white solid with consistent IR, mass and $^1$HNMR spectra data.

Anal. calc'd for C$_{24}$H$_{39}$F$_2$O$_6$Li. 0.75 H$_2$O (MW=482.02):
 C,59.80; H,8.47; F,7.88.
Found: C,59.86; H,8.48; F,7.89.
IR Spectrum (KBr): 3420 cm$^{-1}$ (OH), 1722 cm$^{-1}$ (C=O,ester), 1582 cm$^{-1}$ (C=O, acid salt).
Mass Spectrum: (M+H)$^+$=469, (M+Li)$^+$=475, (M−Li)$^-$=461.
$^1$H-NMR Spectrum (D$_2$O, 270 MHz);
 δ 0.79 (t+d,6H,CH$_3$),
 1.11 (s,6H,CH$_3$),
 3.63 (m,1H,CH—OH),
 4.04 (m,1H, CH—OH)
 5.16 (s,1H, CH—O)ppm.

What is claimed is:

1. A compound of the formula

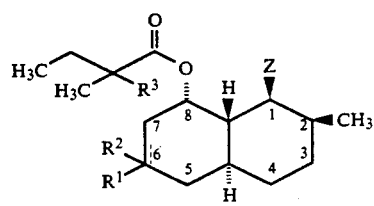

and pharmaceutically acceptable salts and tautomeric mixtures thereof, wherein:
 Z is

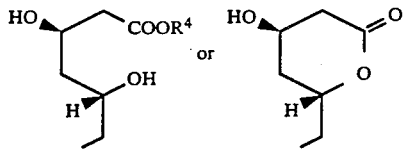

$R^1$ and $R^2$ are each independently fluoro or hydrogen, except that at least one of $R^1$ and $R^2$ is fluoro;

$R^3$ is hydrogen, $C_{1-12}$ alkyl, $C_{6-10}$ aryl which is a monocyclic or a bicyclic aromatic group containign 6 or 10 carbon atoms in the ring portion wherein the ring can be substituted by 1 to 2 lower alkyl groups, 1 to 2 halogen atoms, or 1 or 2 lower alkoxy groups, or $C_{6-10}$ aryl $C_{1-12}$ alkyl; and $R^4$ is hydrogen, $C_{1-12}$ alkyl, ammonium, $C_{1-12}$ alkyl ammonium, or alkali metal;

and wherein carbons 5 to 6 are single- or double-bonded and carbons 6 to 7 are single- or double-bonded, except that carbons 5 to 6 and 6 to 7 are not both double-bonded.

2. The compound of claim 1, wherein $R^3$ is hydrogen $C_1$-$C_6$hd 12 alkyl.

3. The compound of cliam 1, wherein $R^3$ is methyl.

4. The compound of claim 1, wherein $R^1$ is methyl, Z is

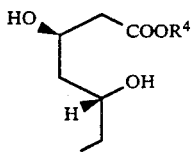

and $R^4$ is hydrogen or alkali metal.

5. The compound of claim 1, wherein $R^1$ is methyl, Z is

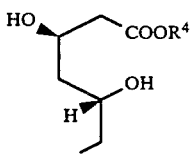

and $R^4$ is lithium.

6. A compound of claim 1 selected from the group consisting of

[1S-[1α,4aα,7β,8β(2S*,4S*),8aβ]]-2-methyl-butanoic acid, 3,3-difluorodecahydro-7-methyl-8--(tetrahydro-4-hydroxy-6-oxo-2H-pyran-2-yl)-ethyl]-1-naphthalenyl ester;

[1S-[1α(βS*,ΔS*),2α,4aβ,8β(R*),8aβ]]-6,6-difluorodecahydro-β,Δ-dihydroxy-2-methyl-8-(2-methyl-1-oxobutoxy)-1-naphthaleneheptanoic acid, monolithium salt;

[1S-[1α(R*),3α,4aα,7β,8β(2S*,4S*),8aβ]]-2-methyl-butanoic acid, 3-fluorodecahydro-7-methyl--[2-[tetrahydro-6-oxo-4-hydroxy-2H-pyran-2-yl]-ethyl]-1-naphthalenyl ester;

[1S-[1α(βS*,ΔS*),2α,4aβ,6β,8β(R*),8aα]]-6-Fluorodecahydro-β,Δ-dihydroxy-2-methyl-8-(2-methyl-1-oxobutoxy)-1-naphthaleneheptanoic acid, monolithium salt;

[1S-[1α(R*),3β,4aα,7β,8β(2S*,4S*),8aβ]]-2-methyl-butanoic acid, 3-fluorodecahydro-7-methyl-8-[2-tetrahydro-6-oxo-4-hydroxy-2H-pyran-2-yl]-ethyl]-1-naphthalenyl ester;

[1S-[1α(βS*,ΔS*),2α,4aβ,6β,8β(R*),8aβ]]-6-Fluorodecahydro-β,Δ-dihydroxy-2-methyl-8-(2-methyl-1-oxobutoxy)-1-naphthaleneheptanoic acid, monolithium salt;

[1S-[1α(R*),3β,4aα,7β,8β(2S*,4S*),8aβ]]-2-methyl-Dimethylbutanoic acid, 3-fluorodecahydro-7-methyl-8-[2-(tetrahydro-4-hydroxy-6-oxo-2H-pyran-2-yl)-ethyl]-1-naphthalenyl ester;

[1S-[1α(βS*,ΔS*),2α,4aβ,6α,8β,8aα]]-8-(2,2-Dimethyl-1-oxobutoxy)-6-fluorodecahydro-β,Δ-dihydroxy-2-methyl-1-naphthaleneheptanoic acid, monolithium salt;

[1S-[1α(R*),4aα,7β,8β(2S*,4S*),8aβ]]-2,2-Dimethyl-butanoic acid, 3,3-difluorodecahydro-7-methyl-8-[2-(tetrahydro-4-hydroxy-6-oxo-2H-pyran-2-yl)ethyl]-1-naphthalenyl ester; and

[1S-[1α(βS*,ΔS*),2α,4aβ,8β,8aα]]-8-(2.2-Dimethyl-1-oxobutoxy)-6,6-difluorodecahydro-β,Δ-dihydroxy-2-methyl-1-naphthalene-heptanoic acid, monolithium salt.

7. A method of inhibiting or treating hypercholesterolemia, which comprises administering to a patient in need of such treatment an effective amount of a compound as defined in claim 1.

8. A method of inhibiting or treating atherosclerosis, which comprises administering to a patient in need of such treatment an effective amount of a compound as defined in claim 1.

9. A hypocholesterolemic or hypolipidemic composition comprising a compound as defined in claim 1 and a pharmaceutically acceptable carrier therefor.

10. A method of inhibiting cholesterol biosynthesis, which comprises administering to a patient in need of such treatment a cholesterol biosynthesis-inhibiting amount of a compound as defined in claim 1.

* * * * *